United States Patent [19]

Janusz

[11] Patent Number: 4,811,430
[45] Date of Patent: Mar. 14, 1989

[54] EYE SHIELD AND HEADBAND COMBINATION

[76] Inventor: Joseph Janusz, 7204 Jacarada Ave., Miami Lake, Fla. 33014

[21] Appl. No.: 131,396

[22] Filed: Dec. 10, 1987

[51] Int. Cl.$^4$ ............................................. A61F 9/02
[52] U.S. Cl. ........................................... 2/452; 2/454; 2/171; 2/DIG. 11
[58] Field of Search .................. 2/171, DIG. 11, 454, 2/452, 10, 426, 173; 351/155, 158

[56] References Cited

U.S. PATENT DOCUMENTS

| | | | |
|---|---|---|---|
| 3,378,851 | 4/1968 | McBrayer | 2/454 |
| 4,393,519 | 7/1983 | Nicastro | 2/DIG. 11 X |
| 4,520,510 | 6/1985 | Daigle | 2/DIG. 11 X |
| 4,616,367 | 10/1986 | Jean, Jr. et al. | 2/DIG. 11 X |
| 4,712,254 | 12/1987 | Daigle | 2/171 |

*Primary Examiner*—Peter Nerbun
*Attorney, Agent, or Firm*—John H. Faro

[57] ABSTRACT

In combination, a frameless optical eye shield and a moisture-absorbent headband. The eye shield is a transparent sheet having one of a pair of loop-and-pile fasteners adhered to the upper margin of its outer surface. The headband has a pocket attached to its inner surface and also the other of said fasteners adhered to the lower margin of its inner surface. The eye shield may be stored in the pocket when it is not in use, and is attached to the headband with the fasteners when it is in use.

6 Claims, 1 Drawing Sheet

EYE SHIELD AND HEADBAND COMBINATION

BACKGROUND OF THE INVENTION

1. Field of the Invention

This invention relates to a novel combination of an eye shield and a headband. The novel combination is particularly adapted to be worn on the head of a user to absorb perspiration from the user's forehead and to provide protection for the user's eyes against solar radiation.

2. Description of the Prior Art

Individuals engaged in active outdoor sports, such as jogging, tennis and handball often wear moisture-absorbent headbands. These headbands usually consist of a stretchable fabric adapted to encircle the head of the user in such a manner as to absorb perspiration from the forehead of the user and to prevent droplets of perspiration from running into the user's eyes. Such headbands do not provide any protection for the user's eyes against solar radiation.

U.S. Pat. No. 4,393,519 to N. J. Nicastro describes a combination of a visor sewn into a headband which offers some protection for the user's eyes against solar radiation. That prior combination includes framed sunglasses and fastener means, such as loop-and-pile fasteners, suitably adapted for detachably attaching the frames of the sunglasses to the visor. That prior combination is bulky and does not provide all the protection that is possible.

OBJECTS OF THE INVENTION

An object of this invention is to provide a novel combination of a headband and a means for shielding the user's eyes against solar radiation.

A further object of this invention is to provide a novel combination of a moisture-absorbent headband and an optical eye shield.

Another object of this invention is to provide a novel combination, as described above, which can absorb perspiration on the forehead of the user and, at the same time, protect the user's eyes against solar radiation.

A further object of this invention is to provide a novel combination, as described above, which is simple in construction and can be fabricated at relatively low cost.

SUMMARY OF THE INVENTION

The novel combination comprises (1) a frameless optical eye shield having an outer eye shield surface and one of a pair of loop-and-pile fasteners attached along an edge of said outer surface, and (2) an annular cloth headband having an inner headband surface and the other of said pair of loop-and-pile fasteners attached along an edge of said inner surface. There is a pocket adapted for housing the eye shield attached to the inner headband surface. The eye shield may be removed from the pocket and detachably attached to the headband with the loop-and-pile fasteners to extend in front of the user's eyes in wrap-around fashion.

The headband is preferably constructed of a stretchable, moisture-absorbent fabric and is otherwise adapted to encircle and conform with the user's head. The pocket is preferably constructed of a stretchable, moisture-absorbent fabric that is sewn to the inner surface of the headband. The other of the fasteners is preferably adhered along the lower edge of the pocket which lies over the lower edge of the headband. The eye shield is preferably curved to conform closely with the user's forehead and to produce the wrap-around feature when it is used.

With the headband positioned on the user's head, perspiration on the user's head is absorbed into the headband and droplets of sweat are prevented from running into the user's eyes. With the eye shield attached to the headband, the user's eyes are protected from both ultraviolet and infrared radiation by the close fit along the headband and the wrap-around feature of the eye shield. The headband may later be detached from the eye shield and washed. Then, the eye shield may be stored in the pocket awaiting subsequent use.

DESCRIPTION OF THE INVENTION INCLUDING PREFERRED EMBODIMENTS

Figure 1:
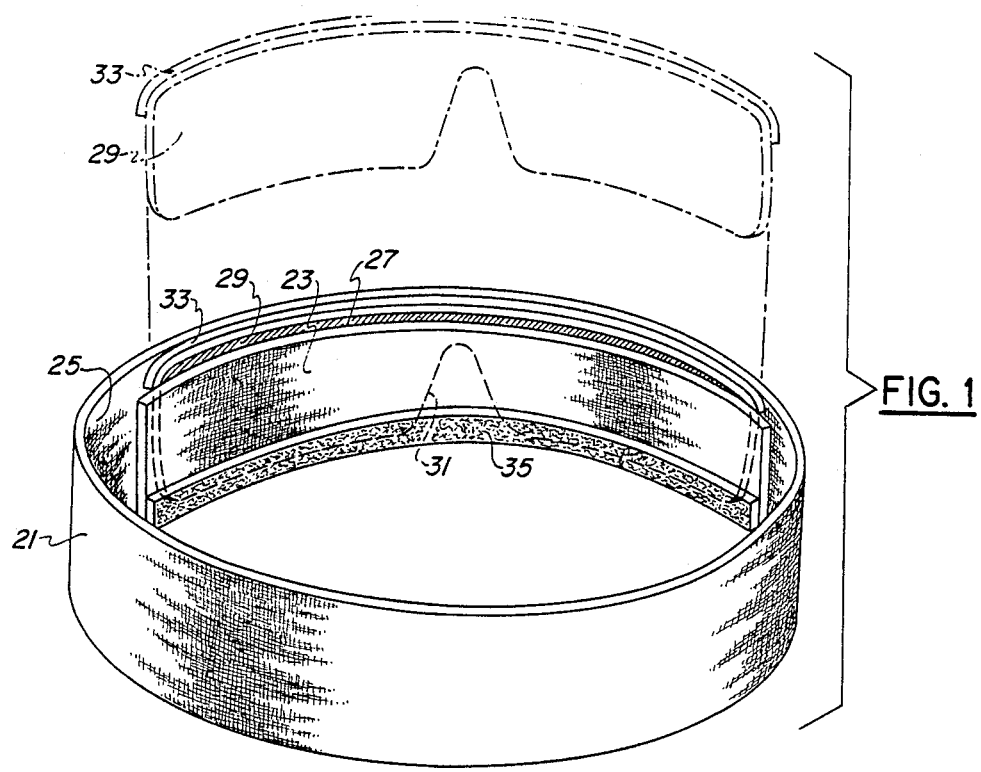
FIG. 1 is a perspective back view of a preferred embodiment of the novel combination.

The following description of some of the preferred embodiments of the concepts of this invention is made in reference to the accompanying figures. Where an individual structural element is depicted in more than one figure, it is assigned a common reference numeral for simplification of identification and understanding.

FIG. 1 shows the novel combination viewed from behind. The novel combination includes an annular cloth band (21) made of a fabric that is highly moisture absorbent and, preferably, has an elastic characteristic so that it can be stretched to slip around, and then can be relaxed to snugly encircle the user's head. The headband (21) should be made of a lightweight fabric that dries relatively rapidly. In this embodiment, the headband is about 7 cm (2.4 inches) wide and is made of a cotton fabric.

A pocket (23) is sewn to the inner surface (25) of the headband (21). The pocket (23) is open along its upper edge (27). The pocket (23) is made of cloth and, preferably, is made of the same material as the headband (21). The pocket (23) is adapted in size to store an eye shield (29).

The eye shield (29) is a planar plastic sheet, that is transparent and of optical quality. The eye shield (29) should be absorbent of portions of the infrared and ultraviolet spectrum that are harmful to the user. The eye shield (29) is cut to a desired size and shape and is curved to fit the forehead of the user and to wrap-around the user's eyes and temples. The eye shield (29) has smooth sides, no protuberances, no frame and is slightly wider than the pocket (23) so that it fits snugly therein. The lower margin of the eye shield (29) has a smooth notch (31) therein to fit comfortably over the user's nose. A typical eye shield is about 7.25 inches wide, about 2.25 inches high and has a curvature along its width of about a 5-inch radius.

The novel combination includes also a pair of loop-and-pile fasteners for attaching the upper margin of the eye shield (29) to the lower margin of the headband (21). Such fasteners are available commercially under the trademark VELCRO. The preferred embodiment shown in FIG. 1, employs as the fasteners two adhesive-backed strips. The one fastener strip (33) with the pile is attached to the upper margin of the outer surface of the eye shield (29) with the adhesive backing of the strip (33). The other fastener strip (35) with the loops is attached to the lower margin of the inner surface (25) of the headband (21) with the adhesion backing of the other strip (35).

When not in use, the eye shield (29) is usually stored in the pocket (23) as shown in FIG. 1. The user can wear the headband (21) with the eye shield (29) in the pocket (23). When the user desires to use the eye shield (29), it is removed from the pocket (23) as shown by the dashed figure, and attached to the headband (21) by overlaying the fasteners (33) and (35) upon one another and then pressing them together gently.

Figure 2:
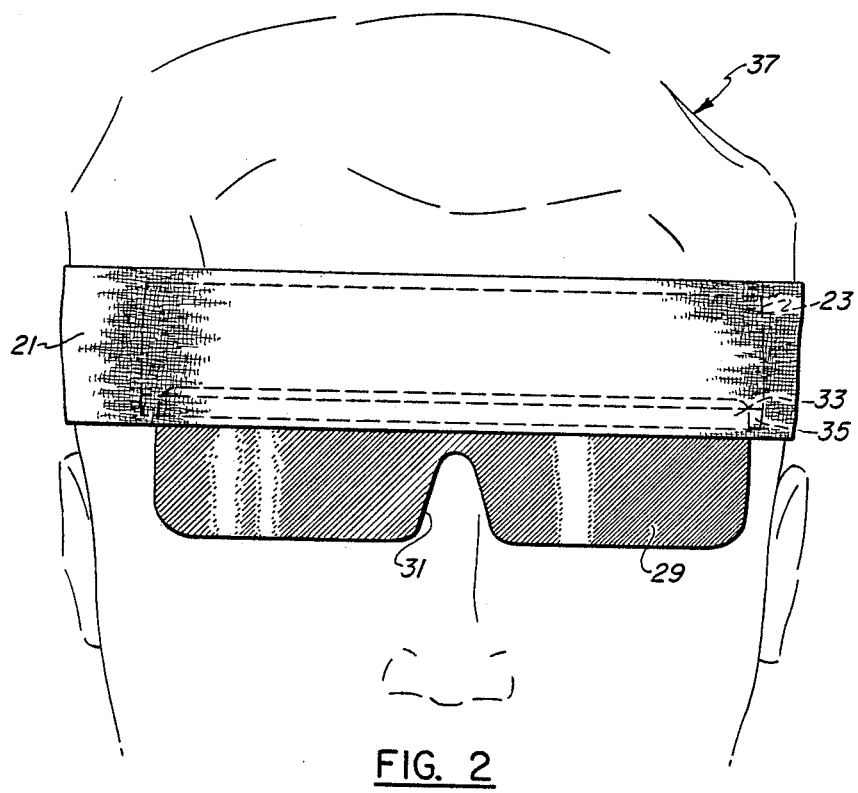
FIG. 2 is a front view of the novel combination shown in FIG. 1 with the eye shield in use by a user.

As shown in FIG. 2, the eye shield (29) hangs down below the headband (21) with the fasteners (33) and (35) one over the other. The headband (21) is stretched, dropped over the head (37) of the user to a position with the pocket (23) over the user's forehead and with the notch (31) over the bridge of the user's nose. In this position, the eye shield (29) is located in front of the user's eyes and wraps around the user's head to block out light coming in from the sides. No light enters from the top of the eye shield since the headband (21) lies over the shield (29). In this position, the headband (21) is stable on the user's head even during vigorous activity by the user. In addition, the headband (21) performs the functions of absorbing perspiration, keeping droplets out of the user's eyes, as well as supporting the eye shield (29). The eye shield (29) can be detached by removing the headband (21) from the user's head and gently pulling apart the headband (21) and the eye shield (29).

The simple construction of the novel combination permits it to be made with low cost materials and a minimum of labor. In addition, the outer surface of the headband (21) can carry an inscription or decoration.

The foregoing figures and descriptions thereof are provided as illustrative of some of the preferred embodiments of the concepts of the invention. While these embodiments represent what is regarded as the best modes for practicing this invention, they are not intended as delineating the scope of the invention, which is set forth in the following claims.

What is claimed is:

1. In combination, a frameless optical eye shield having an upper shield edge and a headband having an upper headband edge and a lower headband edge, said eye shield comprising a transparent planar sheet having an outer eye shield surface and one of a pair of loop-and-pile fasteners attached along said upper shield edge of said outer eye shield surface, and said headband comprising an annular cloth band having an inner headband surface, the other of a pair of loop-and-pile fasteners attached along said lower headband edge of said inner headband surface, and a pocket attached to said inner headband surface, said pocket having an open upper edge and being adapted to house said eye shield.

2. The combination defined in claim 1, wherein said headband is adapted to encircle the head of a user and at least a portion of said headband is constructed of a stretchable, moisture-absorbent fabric, said portion having a section that is adapted to conform closely with the forehead of the user.

3. The combination defined in claim 2, wherein said pocket is constructed of a stretchable, moisture-absorbent fabric, and said pocket is adapted to bear on and conform closely with the forehead of the user.

4. The combination defined in claim 3, wherein said eye shield is a single plastic sheet curved to conform closely with the forehead of the user.

5. The combination defined in claim 4, wherein said headband and said pocket are both entirely made of said stretchable, moisture-absorbent fabric.

6. The combination defined in claim 3, wherein said one loop-and-pile fastener is positioned to mate with said other loop-and-pile fastener whereby said eye shield is detachably securable to said headband.

* * * * *